Figure 1:
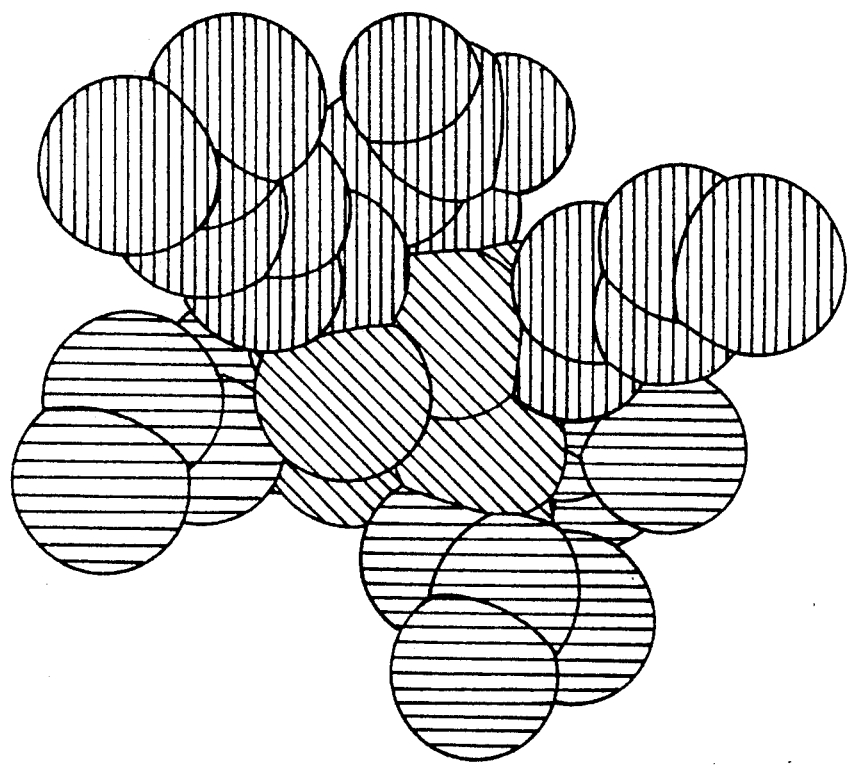

United States Patent [19]

Wei

[11] Patent Number: 5,177,060
[45] Date of Patent: Jan. 5, 1993

[54] ANTI-INFLAMMATORY PEPTIDES AND TREATMENT TO INHIBIT VASCULAR LEAKAGE IN INJURED TISSUES

[75] Inventor: Edward T. Wei, Berkeley, Calif.

[73] Assignee: Regents of the University of California, Oakland, Calif.

[21] Appl. No.: 462,578

[22] Filed: Jan. 9, 1990

[51] Int. Cl.$^5$ ................. A61K 37/00; A61K 37/02; C07K 5/00; C07K 7/00
[52] U.S. Cl. .................................. 514/15; 514/12; 514/14; 530/327; 530/326; 530/325; 530/324
[58] Field of Search ............................. 514/12, 14, 15; 530/324, 325, 326, 327

[56] References Cited

U.S. PATENT DOCUMENTS

| | | |
|---|---|---|
| 3,980,778 | 9/1976 | Ayer et al. |
| 4,404,198 | 9/1983 | Kelley |
| 4,415,558 | 11/1983 | Vale, Jr. et al. |
| 4,489,163 | 12/1984 | Rivier et al. ............ 436/86 |
| 4,528,189 | 7/1985 | Lederis et al. |
| 4,533,654 | 8/1985 | Lederis et al. |
| 4,579,844 | 4/1986 | Rovee et al. |
| 4,594,329 | 6/1986 | Vale, Jr. et al. |
| 4,801,612 | 1/1989 | Wei et al. ............ 514/12 |
| 4,883,863 | 11/1989 | Abe et al. ............ 530/331 |
| 4,895,931 | 1/1990 | Okazaki et al. ............ 530/326 |
| 4,923,963 | 5/1990 | Stewart et al. ............ 530/314 |

OTHER PUBLICATIONS

Rudinger, Peptide Hormones, pp. 1-7, Parsons (ed.) University Park Press, Baltimore, Jun. 1976.

Hoekfelt et al., Chemistry Abstracts, 1988, vol. 108, No. 25, 180219h.

Wei et al., Chemistry Abstracts, 1989, vol. 111, No. 25, 225416a.

Pinckard, et al., "Platelet-Activating Factors", 1988, pp. 139-167, Inflammation: Basic Principles and Clinical Correlates, Raven Press, N.Y.

Persson, "The Role of Microvascular Permeability in Pathogenesis of Asthma", European Jrnl. of Resp. Diseases, 1986, Spplmt. No. 144, vol. 68.

Stern, et al., "Ibuprofen in the Treatment of UV-B-Induced Inflamation", pp. 508-512, Archives of Dermatology, 1985, vol. 121, No. 4.

Melchiorri, et al., "Action of Sauvagine on the Mesenteric Vascular Bed of the Dog", 1981, pp. 1-13, Regulatory Peptides, Elsevier/North-Holland Biomedical Press.

Ling, et al., "Isolation and Characterization of Caprine Corticotropin-Releasing Factor", 1984, pp. 1218-1224, Biochemical and Biophysical Research Communications, vol. 122, No. 3.

Esch, et al., "Isolation and Characterization of the Bovine Hypothalamic Corticotropin-Releasing Factor", 1984, pp. 899-905, Biochemical and Biophysical Research Communications, vol. 122, No. 3.

Patthy, et al., "Isolation and Amino Acid Sequence of Corticotropin-Releasing Factor From Pig Hypothalami", 1985, pp. 8762-8766, Proceedings of the Academy of Sciences, vol. 82, No. 24.

(List continued on next page.)

Primary Examiner—Merrell C. Cashion, Jr.
Assistant Examiner—A. N. Davenport
Attorney, Agent, or Firm—Majestic, Parsons, Siebert & Hsue

[57] ABSTRACT

Relatively small, synthetic anti-inflammatory peptides are provided having the primary sequence $$T_N—A_1—A_2—A_3—A_4—A_5—A_6—T_C$$

in which $T_N$ is an amino acid portion, $A_1$ through $A_6$ each is a synthetic or natural amino acid in the D- or L-configuration, and $T_C$ is a part of or comprises an amidated carboxyl terminal portion. Each of $A_1$, $A_2$ and $A_5$ is a polar amino acid while each of $A_3$, $A_4$ and $A_6$ is a nonpolar amino acid. These relatively small, synthetic peptides inhibit vascular leakage and are usefully administered to mammals for applications such as in the treatment of edema in connection with brain, skin, mucosal and musculature injuries.

4 Claims, 2 Drawing Sheets

OTHER PUBLICATIONS

Montecucchi, et al., "Amino Acid Composition and Sequence Analysis of Sauvagine, A new Active Peptide From the Skin of *Phyllomedusa sauvagei*", 1981, *Int. Journal of Peptide and Protein Research*, pp. 113-120, vol. 18.

Montecucchi, et al., "Secondary Structure Prediction of Sauvagine, a Novel Biologically Active Polypeptide From a Frog", 1982, *Int. Journal of Peptide and Protein Research*, pp. 139-143, vol. 20.

Pallai, et al., "Structural Homology of Corticotropin-Releasing Factor, Sauvagine, and Urotensin I: Circular Dichroism and Prediction Studies", 1983, *Proceedings of the Natl. Acad. Sci.* USA, pp. 6770-6774, vol. 80.

Lau, et al., "Surface Properties of an Amphiphilic Peptide Hormone and of its Analog: Corticotropin-Releasing Factor and Sauvagine", 1983, *Proc. Natl. Sci.* USA, pp. 7070-7074, vol. 80.

Miele et al., "Novel Anti-Inflammatory Peptides From the Region of Highest Similarity Between Uteroglobin and Lipocortin I", 1988, *Nature*, vol. 335.

van Binsbergen et al., "Synthetic Peptide From Lipocortin I Has No Phospholipase $A_2$ Inhibitory Activity", 1989, *FEB*, pp. 293-297, vol. 247.

Vostal et al., "Novel Peptides Derived From A Region of Local Homology Between Uteroglobin & Lipocortin-1 Inhibit Platelet Aggregation & Secretion", 1989, *Biochemical & Biophysical Research Communications*, vol. 165, No. 1.

ANTI-INFLAMMATORY PEPTIDES AND TREATMENT TO INHIBIT VASCULAR LEAKAGE IN INJURED TISSUES

This invention was made with Government support under Grant No. DA-00091 awarded by the National Institutes of Health. The Government has certain rights in this invention.

FIELD OF THE INVENTION

This invention generally relates to anti-inflammatory agents and to uses in reducing inflammatory responses, such as edema in connection with brain, skin, mucosal and musculature injuries, and more particularly to the use of relatively small, synthetic peptides that have the property of inhibiting vascular leakage.

BACKGROUND OF THE INVENTION

Inflammation is signaled by redness, swelling, heat and pain as a reaction of the body against injury or assault. A variety of chemicals have been implicated as chemical mediators of the inflammatory reaction, including histamine, kinins, prostaglandins, platelet-activating factors, leukotrienes, and, from nerve endings, substance P. Mediators of the acute inflammatory reaction seem to play roles in one or more of increasing vascular permeability, attracting leukocytes, producing pain, local edema and necrosis.

A variety of physiologic responses occur from the biological events that constitute the inflammatory processes. For example, Pinckard et al. at Chapter 10 describe platelet-activating factors ("PAF") in the text *Inflammation: Basic Principles and Clinical Correlates* (Gallin et al. Ed. 1988) This family of structurally related compounds appear to promote a variety of physiologic actions that are directly or indirectly related to inflammatory reactions. The authors note that PAF has been implicated in the pathogenesis of human disease conditions such as endotoxin shock and organ transplantation rejection.

Swelling is a characteristic inflammatory response of tissues to injury. Swelling is produced by leakage of water and solutes of the blood directly into the tissue matrix. The increased leakiness of blood vessels after injury may be due to direct damage of blood vessels or may occur after the release of substances such as histamine (inflammatory mediators) that open up gaps between endothelial cells that line the blood vessels. A mild degree of swelling (or edema) does not affect the functional integrity of injured tissues (except perhaps in the brain), but, in severe injuries, massive swelling distorts tissue architecture, impedes the delivery of oxygen to cells, and causes extensive fluid loss from the vascular compartment. Thus, a pharmacological agent capable of inhibiting the swelling process may have therapeutic value in the treatment of tissue injuries.

Inflammation is also involved in various chronic conditions, such as asthma, although it is not presently clear which inflammatory cells or which particular mediators are significantly involved in asthma. Persson, "The Role of Microvascular Permeability in the Pathogenesis of Asthma", *European Journal of Respiratory Diseases*, Supp. No. 144, Vol. 68, pp. 190-204 (1986), concludes that extravasated plasma protein is always present in airways lumen of asthmatic subjects.

There are steroid and non-steroid, anti-inflammatory drugs known to the art. U.S. Pat. No. 4,579,844, inventors Rovee et al., issued Apr. 1, 1986, discloses topically treating an inflammatory condition of the skin by use of the prostaglandin synthetase inhibitor concurrently with a corticosteroid. U.S. Pat. No. 4,404,198, inventor Kelley, issued Sep. 13, 1983, discloses the topical application of a composition including phenyl salicylate to treat inflammation. U.S. Pat. No. 3,980,778, inventors Ayer et al., issued Sep. 14, 1976, discloses a steroid for use in the topical, oral or parenteral treatment of skin and mucous membrane inflammations. Ibuprofen (a known anti-inflammatory agent) has been tested in connection with UV-B-induced inflammation, but was found to have limited usefulness in treating sunburn reaction and is only somewhat more effective than placebo for the relief of symptoms associated with UV-B-induced inflammation after high dose UV-B phototherapy for psoriasis. Stern et al., *Arch. Derm.*, 121, pp. 508-512 (1985).

U.S. Pat. No. 4,801,612, inventor Wei, issued Jan. 31, 1989, discloses the use of inhibiting an inflammatory response in the skin or mucosal membranes of a patient by administering corticotropin-releasing factor or its analogs.

The first corticotropin-releasing factor (CRF, also called CRH or corticoliberin) to be characterized was a 41-residue peptide isolated from ovine hypothalami by Vale et al. (1981). Subsequently, the sequence of human-CRF was deduced from cDNA studies and shown to be identical to rat-CRF. More recently, caprine, bovine, porcine, and white sucker fish CRF have been characterized. The CRF of hoofed animals show considerable differences from man, but the pig and fish sequences differ from the human/rat sequence by only 2 out of 41 residues.

For some mysterious reason, peptides with homologous structures to mammalian CRF are found in cells of certain frog skins and in the urophysis of fish. In fact, the structure of sauvagine, the 40 amino acid peptide isolated from the skins of Phyllomedusa frogs, was reported several years before Vale's description of ovine-CRF. The structure of sucker fish urotensin I was reported just months after the description of ovine-CRF and resulted from an independent line of inquiry by Lederis's group in Canada. Although sauvagine and urotensin I release adrenocorticotropin from the pituitary, the functions of these peptides in the tree-frog (Phyllomedusa species that live in arid regions of South America) and in the sucker fish remain unknown. Recently, it has been shown that the sucker fish has its own hypothalamic CRF which is very close in structure to h/rCRF. Thus, the sucker fish would not require urotensin I for neuroendocrine regulation because it already has CRF in it hypothalamus.

Rat corticotropin-releasing factor (hereinafter "CRF") is described in U.S. Pat. No. 4,489,163, inventors Rivier et al., issued Dec. 18, 1984. The amino acid sequence of both human and rat CRF is illustrated below:

Ser—Glu—Glu—Pro—Pro—Ile—Ser—Leu—Asp—Leu—Thr—
Phe—His—Leu—Leu—Arg—Glu—Val—Leu—Glu—Met—
Ala—Arg—Ala—Glu—Gln—Leu—Ala—Gln—Gln—Ala—His—
Ser—Asn—Arg—Lys—Leu—Met—Glu—Ile—Ile—$NH_2$

U.S. Pat. No. 4,415,558, inventors Vale, Jr. et al., issued Nov. 15, 1983, describes the synthesis of sheep CRF, analogs, and isolation of the oCRF from ovine hypothalamic extracts. The synthetic oCRF was found to lower blood pressure. The amino acid sequence of ovine (sheep) CRF is illustrated below:

```
Ser—Gln—Glu—Pro—Pro—Ile—Ser—Leu—Asp—Leu—
Thr—Phe—His—Leu—Leu—Arg—Glu—Val—Leu—Glu—
Met—Thr—Lys—Ala—Asp—Gln—Leu—Ala—Gln—
Gln—Ala—His—Ser—Asn—Arg—Lys—Leu—Leu—Asp—
Ile—Ala—NH₂
```

The generally similar peptide, sauvagine, was described in Regulatory Peptides 2, 1-13 (1981). Sauvagine is reported to have biological activity in lowering blood pressure in mammals and stimulating the secretion of ACTH and β-endorphin. The amino acid sequence of sauvagine is illustrated below:

```
pGlu—Gly—Pro—Pro—Ile—Ser—Ile—Asp—Leu—Ser—
Leu—Glu—Leu—Leu—Arg—Lys—Met—Ile—Glu—Ile—
Glu—Lys—Gln—Glu—Lys—Glu—Lys—Gln—Gln—Ala—
Ala—Asn—Asn—Arg—Leu—Leu—Leu—Asp—Thr—
Ile—NH₂
```

U.S. Pat. No. 4,528,189, inventors Lederis et al., issued Jul. 9, 1985, and U.S. Pat. No. 4,533,654, inventors Lederis et al., issued Aug. 6, 1985, describe white sucker and carp urotensin I, respectively, as stimulating ACTH and lowering blood pressure. The amino acid sequence of carp urotensin I is illustrated below:

```
H—Asn—Asp—Asp—Pro—Pro—Ile—Ser—Ile—Asp—
—Leu—Thr—Phe—His—Leu—Leu—Arg—Asn—Met—
—Ile—Glu—Met—Ala—Arg—Asn—Glu—Asn—Gln—
—Arg—Glu—Gln—Ala—Gly—Leu—Asn—Arg—Lys—
—Tyr—Leu—Asp—Glu—Val—NH₂
```

The other CRF-related peptide, white sucker urotensin I, has an amino acid sequence the same as the carp urotensin, except the amino acid at the 24 position is isoleucine and the amino acid at the 27 position is glutamic acid.

Ling et al., *BBRC*, Vol. 122, pp. 1218-1224 (1984), disclose the structure of goat CRF, which is the same as that for sheep CRF. Esch et al., *BBRC*, Vol. 122, pp. 899-905 (1984), disclose the structure of bovine CRF which differs from sheep and goat CRF only by one amino acid residue (number 33 which is Asparagine rather than the number 33 Serine of goat and sheep CRF). Porcine CRF has been isolated and characterized by Patthy et al., *Proc. Natl. Acad. Sci.*, Vol. 82, pp. 8762-8766 (1985). Porcine CRF shares a common amino acid sequence (residues 1-39) with rat/human CRF and differs from these only in position 40 and 41. Residue 40 can be either asparagine or isoleucine and residue 41 is phenylalanine-amide.

These related peptides are summarized below (where the amino acids of the primary structure are illustrated by the IUPAC one-letter symbol).

| Peptides of the Corticoliberin Superfamily | |
|---|---|
| CRF (human/rat) | SEEPPISLDL TFHLLREVLE MARAEQLAQQ AHSNRKLMEII* |
| CRF (porcine) | SEEPPISLDL TFHLLREVLE MARAEQLAQQ AHSNRKLMENF* |
| CRF (fish) | SEEPPISLDL TFHLLREVLE MARAEQLAQQ AHSNRKMMEIF* |
| CRF (sheep/goat) | SQEPPISLDL TFHLLREVLE MTKADQLAQQ AHSNRKLLDIA* |
| CRF (cow) | SQEPPISLDL TFHLLREVLE MTKADQLAQQ AHNNRKLLDIA* |
| uro I (sucker fish) | NDDPPISIDL TFHLLRNMIE MARIENEREQ AGLNRKYLDEV* |
| uro I (carp) | NDDPPISIDL TFHLLRNMIE MARNENQREQ AGLNRKYLDEV* |
| sauv. | pEGPPISIDLS LELLRKMIEI EKQEKEKQQA ANNRLLLDTI* |

*represents the amidation at the C-terminus

Both ovine and human/rat CRF have been used in clinical studies on the endocrine function of the pituitary-adrenal axis. Usually, doses of 1 to 5 μg/kg have been injected intravenously to elicit endogenous release of adrenocorticotropin and increases in plasma corticosteroids. Higher doses of 10 μg/kg and 30 μg/kg of ovine-CRF were used by Orth et al. "Effect of synthetic ovine corticotropin-releasing factor. Dose-response of plasma adrenocorticotropin and cortisol.", *J. Clin. Invest*, 71 pp. 587-595 (1983) in the initial assessment of this hormone in man. The non-endocrine effects of this hormone include symptoms such as flushing, shortness of breath and physical signs such as an increase in minute volume, tachycardia (+20%) and possible hypotension. These parameters return to baseline levels within 30 min. and were not considered to be clinically harmful. The relative safety of CRF peptides is illustrated by the fact that CRF has been evaluated in normal children (aged 6-15 years) at a dose of 1 μg/kg administered as an intravenous bolus, as reported by J. L. Ross, et al., "Ovine corticotropin-releasing hormone stimulation test in normal children", *J. Clin. Endocrinol. Metab.*, 62, pp. 390-392 (1986).

However, it would be advantageous to have a peptide shorter than either CRF, sauvagine or urotensin I that is efficacious for reducing vascular leakage. For example, the costs of producing a peptide with seven to twelve amino acid residues would be much less than the costs of producing one that is forty or forty-one residues long because each residue must be added to the next residue in a step-wise fashion. Also, the possibilities of obtaining more selective biological actions or oral/topical activity from shorter peptides are potential advantages to be considered.

SUMMARY OF THE INVENTION

It is an object of the present invention to provide relatively small, synthetic peptides that can be used to inhibit inflammation of the skin, the mucosal membranes, and to decrease the leakage of blood components into the brain tissue and musculature. Skin and mucosal membrane inflammations can occur from thermal (extremes of heat or cold) or radiation injury, or from noxious endogenous or exogenous substances. Leakage of blood components into the brain tissue, a condition called vasogenic edema of the brain, can be produced by various adverse medical conditions, such as brain ischemia, brain infarction, intracranial hemorrhage from neurosurgical operations, and so forth.

In one aspect of the present invention, an anti-inflammatory peptide is provided having the primary sequence $T_N$—$A_1$—$A_2$—$A_3$—$A_4$—$A_5$—$A_6$—$T_C$ in which $T_N$ is an amino terminal portion having a molecular weight less than about 600 daltons, $A_1$ through $A_6$ each is an amino acid (synthetic or natural) and together $A_1$ through $A_6$ constitute an active core effective in providing anti-inflammatory activity to the peptide, and $T_C$ is part of or comprises an amidated carboxyl terminal portion.

$T_N$ is selected or modified to convey resistance against enzymatic degradation of the active core. Each of $A_1$, $A_2$ and $A_5$ is a polar amino acid in the D- or L-configuration and together $A_1$, $A_2$ and $A_5$ constitute a hydrophilic region for the secondary structure of the peptide. Each of $A_3$, $A_4$ and $A_6$ is a nonpolar amino acid in the D- or L-configuration and together $A_3$, $A_4$ and $A_6$ constitute a hydrophobic region for the secondary structure of the peptide. $T_C$ is an amino group or an amidated amino acid.

The class of anti-inflammatory peptides having the above-described primary sequence are sometimes hereinafter called "nocifensins" because they defend tissue against noxious stimuli and can be used as anti-inflammatory agents.

A therapeutically effective amount of an inventive nocifensin peptide can be administered, preferably by intravenous, intradermal or subcutaneous means, such as in doses from about 1 to about 200 μg/kg. Such administrations reduce the permeability of brain and central nervous system blood vessels and are of therapeutic value in the treatment of tissue injury, such as brain and central nervous injuries. Administrations also provide clinical benefits when used to limit or minimize leakage of blood constituent into tissue during surgery, to alleviate pain and discomfort, and to prevent further swelling for patients already experiencing inflammation.

BRIEF DESCRIPTION OF THE DRAWINGS

In the drawings:

FIG. 1 illustrates a spaced-filling model of a synthetic peptide embodiment for the invention where the model is being viewed from the N-terminus down the axis, or backbone, towards the C-terminus; and, FIG. 2 plots the data from a bioassay conducted with the prior art human/rat CRF and four inventive peptide embodiments, respectively, and illustrates vascular leakage inhibition in a dose related manner (horizontal axis) with respect to saline controls (vertical axis).

DETAILED DESCRIPTION OF THE PREFERRED EMBODIMENTS

When the brain is injured such as in brain ischemia, or infarction, then vasogenic edema occurs and the increased amounts of water compress and distort brain tissue architecture and impede the delivery of oxygen to brain cells. The patient can lose consciousness and stop breathing. When the skin or a mucosal surface is injured by extreme heat or cold, by radiation or assaulted by noxious substances, it is converted from a condition of balanced fluid exchange to a state in which serum and its solutes freely pass into the surrounding tissues. In general, substances are released, either from nerve endings or from cells within the injured tissue, that produce increased vascular permeability. Fluids and proteins in the blood then move from the vascular compartment to the tissue compartment with pain, swelling and tissue damage as a result.

In the present invention, a nocifensive peptide (or a salt form thereof) can be used to inhibit inflammation of a mammal's skin, mucosal membranes, or where there have been (or will be) lacerations of the musculature or injury to the brain. Administration can include intravascular, oral or topical means at dosages of between about 0.001 to 5 mg/kg body weight. However, administration is preferably by intravenous, intradermal, or subcutaneous injection with at least a single dose being given, preferably from about 1 to about 200 μg/kg body weight, and can be about two hours before deliberate lacerations of the musculature (such as during abdominal or orthopedic surgery) and can be up to three days after surgery or accidental injury. Administration is most preferably via the blood stream, but local injections into the cerebrospinal fluid, brain, or into the muscle can be used.

Because the nocifensive peptides have the property of inhibiting vascular leakage from tissues, they are useful in a number of different therapeutic applications. Specific tissues for which clinical usage of these peptides may be applied include skin and mucosal membranes (eyelids, nasal membranes, oropharyngeal membranes, upper respiratory tract, esophagus, lower digestive tract), skeletal muscle, smooth muscle, cardiac muscle, blood vessels of the brain, and blood vessels of the lungs and kidneys. For example, therapeutic uses of these peptides include administration to treat thermal burns, irradiation burns, frostbite, or for other inflammatory conditions of the skin. The peptides may be used to reduce swelling, pain, and plasma extravasation. For irritants deposited on the upper airways or in chronic allergic conditions such as asthma, the peptides may be used to decrease irritancy, bronchial inflammation, edema and plasma extravasation. For lacerative or traumatic injuries to all tissues, such as might occur after knife wounds, surgical operations, and automobile accidents, the peptides may be used to reduce swelling, pain, and inflammation. For tissue infarcts, which result in tissue hypoxia, ischemic anoxia and edema, such as occur after brain strokes or myocardial infarcts, the peptides may be used to reduce passage of blood constituents into the tissue matrix and enhance survival of the remaining tissues. For preventing the actions of endogenous or exogenous chemicals that directly injure the endothelium, such as endotoxins or inflammatory mediators, resulting in the clinical condition of septic shock, the peptides may be useful in reducing the loss of blood volume. Administration may be used for preserving the integrity of the vascular tree of an organ prior to or during its removal for transplantation, such organs being kidneys, liver, or heart.

The nocifensive peptides may be administered in combination with a pharmaceutically acceptable carrier, such as isotonic saline, phosphate buffer solution or the like. Topical administration is also feasible since the peptides are relatively small.

Compositions and excipients useful for the administration of small peptides through the nasal mucosa are, for example, described by U.K. patent application No. 8719248, published Feb. 24, 1988, applicant Sandoz Limited. Topical compositions with enhanced penetration through intact skin preferably include a potentiator, many of which are described by U.S. Pat. No. 4,091,090, issued May 23, 1978, inventor Sipos. The nocifensive peptides form pharmaceutically acceptable salts with organic and inorganic acids and can be administered in salt form. Examples of suitable acids for the formation of pharmaceutically acceptable salts are hydrochloric, sulfuric, phosphoric, acetic, benzoic, citric, malonic, salicylic, malic, fumaric, succinic, tartaric, lactic, gluconic, ascorbic, maleic, benzenesulfonic, methane- and ethanesulfonic, hydroxymethane- and hydroxyethane- sulfonic.

Salts may also be formed with suitable organic pharmaceutically acceptable base addition salts. These organic bases form a class whose limits are readily understood by those skilled in the art. Merely for purposes of illustration, the class may be said to include mono-, di-, and trialkyamines, such as methylamine, dimethylamine, and triethylamine; mono-, di- or trihydroxyalkylamines such as mono-, di- and triethanolamine; amino acids such as arginine, and lysine; guanidine; N-methylglucosamine; N-methylglucamine; L-glutamine; N-methylpiperazine; morpholine; ethylenediamine; N-benzylphenethylamine; tris(hydroxymethyl)aminomethane; and the like. (See for example, "Pharmaceutical Salts," *J. Pharm. Sci.* 66 (1): 1–19 (1977).

Nocifensive peptides of the invention have the primary sequence $T_N$—$A_1$—$A_2$—$A_3$—$A_4$—$A_5$—$A_6$—$T_C$. Thus, the amino terminal, or $T_N$, has a molecular weight less than about 600 daltons and is selected or modified to convey resistance against enzymatic degradation of the active core for the inventive peptide. Preferred moieties for $T_N$ are di-, tri-, tetra-, or penta-peptides or derivatives thereof. Particularly preferred for $T_N$ are D-asparagine, D-tyrosine or D-glutamine. Particularly preferred derivatives for $T_N$ are N-methylphenylalanine or pyroglutamic acid. Other examples of moieties useful to convey resistance against enzymatic degradation are p-chloro-or p-nitro-phenylalanine, lower alkyl alkylated arginine and lysine, and the o-ethyl ethers of asparagine and glutamine. Unnatural amino acids to stabilize or to increase potency and prolong duration of action are illustrated, for example by the article of Nestor et al., *Jour. of Medic. Chem.*, 31 (1), pp. 65-72 (1988).

$A_1$ and $A_2$ are each a basic polar amino acid (synthetic or natural). Thus, $A_1$ and $A_2$ can be in the D- or L-configuration and each is preferably selected from arginine and lysine.

Each of $A_3$, $A_4$ and $A_6$ is a basic non-polar amino acid preferably selected from leucine, isoleucine and methionine, while $A_5$ is an acidic polar amino acid, preferably glutamic acid and aspartic acid.

The six amino acid residues, $A_1$ through $A_6$, together constitute an active core for the peptide that is effective in providing anti-inflammatory activity to the peptide. Since each of $A_1$, $A_2$, and $A_5$ is a polar amino acid (in the D- or L- configuration), together $A_1$, $A_2$, and $A_5$ constitute a hydrophilic region for the secondary structure of the peptide. Since each of $A_3$, $A_4$, and $A_6$, is a nonpolar amino acid (in the D- or L-configuration), together $A_3$, $A_4$, and $A_6$ constitute a hydrophobic region for the secondary structure of the peptide. When the active core is a mixture of D- and L-configurations, then they are believed to form a "random coil". However, when all are, for example, in the L- configuration, then they are believed to form an α-helix. In either event, because the three polar residues will associate together, as will the three hydrophobic residues, the molecules have an amphiphilic character.

Turning to FIG. 1, a space-filling model of a particularly preferred embodiment is illustrated where the red hatching represents polar residues while the blue hatching represents hydrophobic residues. The model is viewed from the N-terminus down the axis of the molecule. Reading clockwise in the hydrophilic region, $A_1$ illustrated as arginine, $A_5$ as glutamic acid, and $A_2$ as lysine. Reading counter-clockwise in the hydrophobic region, we see illustrated $A_4$ as methionine, $A_3$ as leucine, and $A_6$ as isoleucine. Thus, the particularly preferred peptide embodiment being illustrated has the primary structure:

$T_N$—R K L M E I—$T_C$ where $T_C$ is D-leucineamide and $T_N$ is no particular A.A.

FIG. 1 also illustrates that the hydrophobic and the hydrophilic regions of the inventive peptides each radially outwardly extends from a backbone of the active core with the hydrophilic region and the hydrophobic region being generally opposed. That is, the polar residues do not interdigitate with the hydrophobic residues.

It is believed possible to vary the just-described residues by substitution of either the second basic residue (that is, $A_2$), the acidic residue ($A_5$) or the third hydrophobic residue ($A_6$) with D- or L-asparagine or glutamine, although potency is a likely to be diminished. However, replacement of the acidic residue with asparagine or glutamine may increase the stability of the molecule because the acidic carboxyl ligand would no longer be available to react with the basic amino ligand of the arginine or lysine residues.

Finally, $T_C$ is an amino group or an amidated amino acid. A preferred amidated amino acid is D-leucine amide because this residue is resistant to enzymatic degradation from the C-terminus. A non-polar aromatic residue such as phenylalanine is also a suitable moiety for $T_C$.

The nocifensin peptides can be synthesized by various suitable chemical methods, preferably by solid phase synthesis, manual or automated, as first developed by R. B. Merrifield and described by J. M. Stewart and J. D. Young in "Solid Phase Peptide Synthesis" (1984). Chemical synthesis joins the amino acids in the predetermined sequence starting at the C-terminus. Basic solid phase methods require coupling the C-terminal protected alpha-amino acid to a suitable insoluble resin support. The described nocifensin peptides require benzyhydrylamine (BHA) or 4-methylbenzyhydrylamine (MBHA) resins to produce the C-terminal amide upon completion. Amino acids for synthesis require protection on the alpha-amino group to ensure proper peptide bond formation with the preceding residue (or resin support). Following completion of the condensation reaction at the carboxyl end, the alpha-amino protecting group is removed to allow the addition of the next residue. Several classes of alpha-protecting groups have been described, see J. M. Stewart and J. D. Young in "Solid Phase Peptide Synthesis" (1984), with the acid labile, urethane-based tertiary-butyloxycarbonyl (Boc) being the historically preferred. Other protecting groups, and the related chemical strategies, may be used, including the base labile 9-fluorenylmethyloxycarbonyl (FMOC). Also, the reactive amino acid side-chain functional groups require blocking until the synthesis is completed. The complex array of functional blocking groups, along with strategies and limitations to their use, have been reviewed by M. Bodansky in "Peptide Synthesis" (1976), and, J. M. Stewart and J. D. Young in "Solid Phase Peptide Synthesis" (1984).

Solid phase synthesis is initiated by the coupling of the described C-terminal alpha-protected amino acid residue. Coupling requires activating agents, such as dicyclohexycarbodiimide (DCC) with or without 1-hydroxybenzo-triazole (HOBT), diisopropylcarbodiimide (DIIPC), or ethyldimethylaminopropylcarbodiimide (EDC). After coupling the C-terminal residue, the alpha-amino protecting group is removed by trifluoroacetic acid (25% or greater) in dichloromethane in the case of acid labile tertiary-butyloxycarbonyl (Boc) groups. A neutralizing step with triethylamine (10%) in dichloromethane recovers the free amine (versus the salt). After the C-terminal residue is added to the resin, the cycle of deprotection, neutralization and coupling, with intermediate wash steps, is repeated in order to extend the protected peptide chain. Each protected amino acid is introduced in excess (three to five fold) with equimolar amounts of coupling reagent in suitable solvent. Finally, after the completely blocked peptide is assembled on the resin support, reagents are applied to cleave the peptide from the resin and to remove the side chain blocking groups. Anhydrous hydrogen fluoride (HF) cleaves the acid labile tertiary-butyloxycarbonyl (Boc) chemistry groups. Several nucleophilic scavengers, such as dimethylsulfide and anisole, are included to avoid side reactions especially on side chain functional groups.

A number of the inventive nocifensin peptides have been synthesized and tested by means of a bioassay for anti-inflammatory activity. The synthesis of a particularly preferred one of these peptides is specifically described by Example 1. Example 2 then describes the bioassay procedure used with Table 1 summarizing a number of these peptides and Table 2 showing comparative dose response data.

EXAMPLE 1

The synthesis of an inventive nocifensin peptide having the formula:

D-Ala.His.Ser.D-Asn.Arg.Lys.Leu.Met.Glu.Ile.D-Leu-NH$_2$ was conducted sequentially from the C-terminal amide end on a 4-methylbenzhydrylamine hydrochloride resin (MBHA HCl resin), as commercially available with amine substitution range of 0.4 to 0.6 millimoles per gram resin (CalBiochem, Inc., Bachem, Inc.). The amount of resin equal to one millimole of active amine was washed with appropriate solvents (dichloromethane and/or methanol). Neutralization of the MBHA resin with triethylamine (TEA) in dichloromethane (DCM) removed the salt form, enabling sequential addition of the tertiary-butyloxycarbonyl (Boc) protected amino acid derivatives. The C-terminal residue, Boc-leucine (monohydrate), was coupled to the reactive resin amine groups with one molar dicyclohexycarbodiimide (DCC) in dichloromethane (DCM). Generally equimolar amounts of coupling agent (DCC) and Boc-amino acid are added in excess (five-fold) relative to the resin. The Boc-amino acids are dissolved in dichloromethane (DCM) and/or dimethylformamide (DMF), depending on the particular residue's solubility.

After acidic deprotection with trifluoroacetic acid solution (25% in dichloromethane) and neutralization with triethylamine (10%) in dichloromethane, the stepwise building continued toward the amino end. Boc-arginine (Tos), Boc-histidine (Tos) and Boc-D-asparagine were coupled in a 9:1 mixture of dimethylformamide (DMF) and dichloromethane (DCM). P-toluenesulfonyl (Tos) groups are used to protect the guanidino of arginine and the imidazole of histidine. A xanthyl (Xan) ring was used to protect the amido group of asparagine. 2-Chlorobenzyloxycarbonyl (2-Clz) was used for the lysine side chain. The benzyl ether (Bzl) was used with the hydroxyl of serine, and the benzyl ester (OBzl) used for blocking the carboxyl of glutamic acid.

Finishing the protected amino acid couplings, gave the following intermediate: Boc-D-Ala.His(Tos).Ser(Bzl).D-Asn(Xan).Arg(Tos).Lys(2Clz).Leu.Met.Glu(OBzl).Ile.D-Leu-resin support. The final cleavage and deprotection of the protected peptide resin required acidolysis with hydrogen fluoride (HF), the nucleophilic scavengers dimethylsulfide and anisole (or equivalent) and was done at 0° C. for 30 minutes. Preferably, cleavages at a preliminary lower temperature, 0° C. for 20 minutes, followed by 0° C. for 30 minutes to decrease the probability of side reactions. Alternately, a "low HF" procedure requiring higher concentrations of dimethyl sulfide relative to hydrogen fluoride (3:1 by volume) at 0° C. for three hours may precede normal HF cleavage with MBHA and BHA resins to avoid side reactions.

Removal of the HF under vacuum in the cleavage apparatus precedes multiple washes of the peptide-resin with dry ethyl ether and/or chloroform for extraction. Filtration follows with one molar aqueous acetic acid, with the obtained filtrate frozen and lyophilized. The used resin is weighed to determine the yield of peptide, and the need for any re-extraction.

Example 1 illustrates the synthesis of a preferred embodiment (D-a-H-S-n-R-K-L-M-E-I-l-NH$_2$). A series of the nocifensive peptides have been similarly synthesized and tested. The approximate purity of the peptides prepared ranged from about 57% to 94% (as determined by HPLC). Amino acid sequences and purity data, are set out in Table 1 for a number of these inventive compounds.

The abbreviations used in the table on bioassay results and elsewhere in this disclosure are: standard single letter codes for amino acids, and the lower case of the single letter represents the D configuration of the amino acid. All peptides were synthesized with the carboxylamide terminus or other than carboxylic acid. By "pE" is meant pyroglutamyl, "M°" means methionine sulfoxide, and "Fm" means N-methylphenylalanine.

EXAMPLE 2

The peptides were synthesized by solid phase methods as described or analogous to that described by Example 1, and the approximate purity of most was obtained by high-pressure liquid chromatography and is given in the Table 1. The peptides were dissolved either in saline or an inert dextrin solvent (Molecusol) and injected intravenously into a pentobarbital-anesthetized rat. The rat's hind paw was then immersed in 58°–60° C. water for 1 min and the increase in paw weight, as an index of edema and swelling, was measured 30 min. later. For some peptides, the ability of the substances to inhibit vascular leakage after muscle injury was also tested. Normally, the paw weight of saline-treated animals (controls) will increase by about 68–81% after heat injury. The increase in weight is relative to the contralateral non-heated paw.

In screening the bioactivity of new peptides, a dose of 5 mg/kg i.v. was initially used. In later studies, when greater activity was expected, a screening dose of 1 mg/kg i.v. was used. For peptides that exhibited particularly significant activity, a full dose-response analysis was conducted according to the method of Litchfield and Wilcoxon.

Thus, each peptide was injected intravenously (at the amounts specified, usually 1 or 5 mg/kg, or by full dose-response analysis) 10 min before immersion of the right paw in 58° C. water for 1 min, and weights of both paws were obtained 30 min later. To obtain statistical accuracy, a minimum of six animals were used in each group. The % wt increase was calculated as (wt of heated paw/ wt of unheated paw) ×100 and converted to % of the saline control group values, which were run concurrently. The weight of the paws of the saline-treated animals did not increase after immersion in room temperature (22° C.) water, but increased by 68 to 81% after heat.

TABLE 1

Inventive Peptides (Primary Structure) | HPLC Peak % | % Saline Value
--- | --- | ---
L E L L R K M I E I E# | 62 | 36 ± 4 (at 5.0 mg/kg)
I E L L R K M I E I e# | 73 | 52 ± 6 (at 5.0 mg/kg)
a H n R K L M$^o$ E I | 84 | 86 ± 4 (at 5.0 mg/kg)
a H n R K L M E I | 83 | 49 ± 4 (at 5.0 mg/kg)
a S n R K L L E I | 89 | 59 ± 4 (at 5.0 mg/kg)
F$^m$ n R K L M E I I | 94 | 34 ± 4 (at 1.0 mg/kg)
A A L n R K L L E E A | na | 89 ± 3 (at 5.0 mg/kg)
A H S N R K L M E I I | na | 60 ± 7 (at 5.0 mg/kg)
a H S n R K L I E I I | 87 | 52 ± 4 (at 1.0 mg/kg)
a H S n R K L M Q I I | 92 | 49 ± 4 (at 1.0 mg/kg)
a H S n R K M M E I I | 87 | 46 ± 3 (at 1.0 mg/kg)
A H S N R K L M E N F | 88 | 77 ± 4 (at 5.0 mg/kg)
A H S N R K I M E I I | na | 53 ± 3 (at 5.0 mg/kg)
a H S n R K L M Q n F | 86 | 37 ± 5 (at 5.0 mg/kg)
a H S n R K L M$^o$ E I I | 88 | 36 ± 3 (at 5.0 mg/kg)
pE A H S n R K L M E I I | na | 23 ± 3 (at 5.0 mg/kg)
(1) a H S n R K L M E I I | 79 | 36 ± 4 (at 1.0 mg/kg)
(2) a H S N R K L M E I I | 83 | 28 ± 5 (at 1.6 mg/kg)
(3) a H S n R R L M E I I | 80 | 25 ± 2 (at 1.2 mg/kg)
(4) a H S n R K L L E I I | 81 | 19 ± 2 (at 0.4 mg/kg)
a H S n R K L M D I I | 73 | 70 ± 2 (at 1.0 mg/kg)
a H S n r K L M E I I | 58 | 47 ± 4 (at 1.0 mg/kg)
a H S q R K L M E I I | 69 | 38 ± 6 (at 1.0 mg/kg)
a H S n R K L M e I I | 85 | 24 ± 4 (at 1.0 mg/kg)
a H S n R k L M E I I | 94 | 31 ± 5 (at 1.0 mg/kg)
a H S n R K I I E I I | 94 | 24 ± 7 (at 1.0 mg/kg)
I H A Y R K L L E G e | 84 | 86 ± 3 (at 1.0 mg/kg)
a H A y R K L L E I I | 82 | 35 ± 6 (at 1.0 mg/kg)
I A T y R K L L E I I | 70 | 30 ± 5 (at 1.0 mg/kg)

lower case denotes the D-amino acid
# means Peptide dissolved in 22% dextrin solvent (Molecusol)
M$^o$ = methionine sulfoxide. F$^m$ = N-methylphenylalanine. pE = pyroglutamic acid
(1), (2), (3), and (4) = note these four are further described in Table 2

Turning to the data of Table 1, we see that 29 different nocifensive peptides were prepared and shown to provide a statistically significant inhibition of edema when administered to mammals whose paws were exposed to an inflammation causing situation. Many of these nocifensive peptides provided a remarkable diminution of swelling. Since "100%" under the "% Saline Value" of Table 1 means no diminution of swelling, then peptides such as that having the primary structure "a H S n R K L L E I I" (with a value of 19% saline value when administered at 0.4 mg/kg), "a H S n R K L M e I I" (at 24% saline value) and "a H S n R K I I E I I" (at 24% saline value), in addition to the others designated (1)–(3), are particularly worthy of special note in substantially preventing swelling. The four inventive analogs indicated by the (1)–(4) designations were then further analyzed, as shown by the data of Table 2, for bioactivity and can be compared to the known human/rat CRF.

TABLE 2

Figure 2:
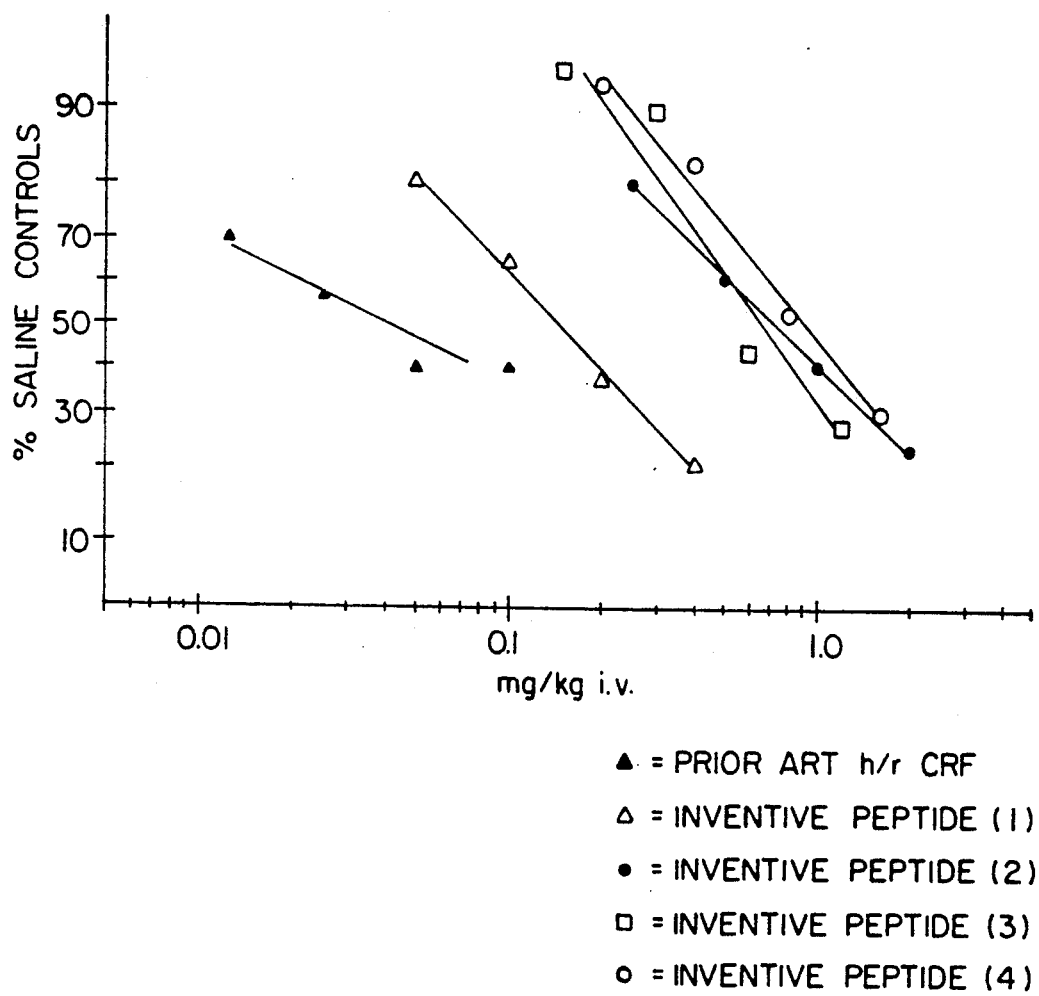

Peptide # for FIG. 2 | Primary Structure | ED50 (95% Confidence) Mg/kg i.v. | Slope | Potency
--- | --- | --- | --- | ---
 | h/rCRF | 0.013 (.002–.089) | 32.0 | 
(1) | a H S n R K L M E I I | 0.12 (.06–0.25) | 3.6 | 1
(2) | a H S N R K L M E I I | 0.56 (.28–1.13) | 2.4 | 1/5
(3) | a H S n R R L M E I I | 0.63 (.29–1.39) | 4.1 | 1/5
(4) | a H S n R K L L E I I | 0.72 (.36–1.44) | 2.9 | 1/6

Log-Probit analysis according to Litchfield and Wilcoxon (1949).

Turning to Table 2 and FIG. 2, we see that the slope value of the prior known human/rat CRF is greater than, and not parallel to, that of the nocifensin peptides. This means it is likely that human/rat CRF acts in a different manner from the nocifensins. The maximum inhibition of swelling obtained with h/r CRF was 64%, whereas with the nocifensins it was greater than 80%. Thus, the nocifensins appear to be considerably more efficacious in reducing vascular leakage than the prior known h/r CRF.

In sum, the inventive nocifensins should find use in treating injured tissues such as involved in stroke (brain tissue), burn or frostbite injury (skin tissue), asthma (mucosa), and surgery (abdominal and/or orthopedic muscles).

It is to be understood that while the invention has been described above in conjunction with preferred specific embodiments, the description and examples are intended to illustrate and not limit the scope of the invention, which is defined by the scope of the appended claims.

I claim:

1. A peptide having the primary structure:

$$T_N-A_1-A_2-A_3-A_4-A_5-A_6-T_C$$

where $T_N$ is an amino terminal portion having a molecular weight less than about 600 daltons and is selected to convey resistance against enzymatic degradation, $T_C$ is D-leucineamide or phenylalanine,
$A_1$ is D- or L- arginine or lysine,
$A_2$ is D- or L- arginine or lysine,
$A_3$ is D- or L- methionine, leucine or isoleucine,
$A_4$ is D- or L- isoleucine, leucine, or methionine,
$A_5$ is D- or L- glutamic acid, glutamine, or aspartic acid, and
$A_6$ is D- or L- isoleucine, leucine, or asparagine.

2. The peptide as in claim 1 wherein:
$T_N$ is a di-, tri-, tetra- or penta-peptide or a derivative thereof.

3. The peptide as in claim 2 wherein:
$T_N$ includes D-asparagine, D-tyrosine or D-glutamine adjacent to the amino acid at $A_1$.

4. The peptide as in claim 2 wherein:
the derivative includes N-methylphenylalanine or pyroglutamic acid.

* * * * *